United States Patent [19]
Kensey et al.

[11] Patent Number: 6,152,888
[45] Date of Patent: Nov. 28, 2000

[54] VISCOSITY MEASURING APPARATUS AND METHOD OF USE

[75] Inventors: Kenneth Kensey; John E. Nash, both of Chester Springs; Harold E. Clupper, West Chester, all of Pa.

[73] Assignee: Visco Technologies, Inc., Exton, Pa.

[21] Appl. No.: 09/400,501

[22] Filed: Sep. 21, 1999

Related U.S. Application Data

[62] Division of application No. 08/919,906, Aug. 28, 1997, Pat. No. 6,019,735.

[51] Int. Cl.⁷ ........................................................ A01B 5/00
[52] U.S. Cl. ............................................. 600/573; 600/486
[58] Field of Search ................................... 600/573, 587, 600/585, 486, 485

[56] References Cited

U.S. PATENT DOCUMENTS

| | | |
|---|---|---|
| H93 | 7/1986 | Matta et al. . |
| 1,810,992 | 6/1931 | VonDallwitz-Wegner . |
| 2,343,061 | 2/1944 | Irany . |
| 2,696,734 | 12/1954 | Brunstrum et al. . |
| 2,700,891 | 2/1955 | Shafer . |
| 2,934,944 | 5/1960 | Eolkin . |
| 3,071,961 | 1/1963 | Heigl et al. . |
| 3,116,630 | 1/1964 | Piros . |
| 3,137,161 | 6/1964 | Lewis et al. . |
| 3,138,950 | 6/1964 | Welty et al. . |
| 3,277,694 | 10/1966 | Cannon et al. . |
| 3,286,511 | 11/1966 | Harkness . |
| 3,342,063 | 9/1967 | Smythe et al. . |
| 3,435,665 | 4/1969 | Tzentis . |
| 3,520,179 | 7/1970 | Reed . |
| 3,604,247 | 9/1971 | Gramain et al. . |
| 3,666,999 | 5/1972 | Moreland, Jr. et al. . |
| 3,680,362 | 8/1972 | Geerdes et al. . |
| 3,699,804 | 10/1972 | Gassmann et al. . |
| 3,713,328 | 1/1973 | Aritomi . |
| 3,720,097 | 3/1973 | Kron . |
| 3,782,173 | 1/1974 | Van Vessem et al. . |
| 3,839,901 | 10/1974 | Finkle et al. . |
| 3,853,121 | 12/1974 | Mizrachy et al. . |
| 3,864,962 | 2/1975 | Stark et al. . |
| 3,908,441 | 9/1975 | Virloget . |
| 3,911,728 | 10/1975 | Fixot . |
| 3,952,577 | 4/1976 | Hayes et al. . |
| 3,967,934 | 7/1976 | Seitz et al. . |
| 3,990,295 | 11/1976 | Renovanz et al. . |
| 3,999,538 | 12/1976 | Philpot, Jr. . |
| 4,083,363 | 4/1978 | Philpot, Jr. . |
| 4,149,405 | 4/1979 | Ringrose . |
| 4,165,632 | 8/1979 | Weber et al. . |
| 4,193,293 | 3/1980 | Cavallari . |
| 4,207,870 | 6/1980 | Eldridge . |
| 4,302,965 | 12/1981 | Johnson et al. . |

(List continued on next page.)

FOREIGN PATENT DOCUMENTS

| | | |
|---|---|---|
| 654 286 A1 | 5/1995 | European Pat. Off. . |
| 2 704 151 | 10/1994 | France . |
| WO 94/20832 | 9/1994 | Germany . |

OTHER PUBLICATIONS

Fibrinogen, Viscosity and White Blood Cell Count Are Major Risk Factors for Ischemic Heart Disease, Yarnell, et al. Mar. 1991, Circulation vol. 83, No. 3.

(List continued on next page.)

*Primary Examiner*—Cary O'Connor
*Assistant Examiner*—Pamela Wingood
*Attorney, Agent, or Firm*—Caesar, Rivise, Bernstein, Cohen & Pokotilow, Ltd.

[57] ABSTRACT

A blood viscosity measuring system and method that monitors the rising head of a column of fluid representing a living being's blood in-vivo to determine the blood viscosity over a range of shears. The system includes a capillary tube, at least a portion of which is located within the vascular system of the being, and a riser tube, having a liquid therein coupled to the capillary tube. A sensor and associated microprocessor are provided to determine the change in the height of the liquid in the riser tube at plural points along the length of the tube from which the viscosity is calculated.

23 Claims, 12 Drawing Sheets

U.S. PATENT DOCUMENTS

| | | |
|---|---|---|
| 4,341,111 | 7/1982 | Husar . |
| 4,417,584 | 11/1983 | Cathignol et al. . |
| 4,426,878 | 1/1984 | Price et al. . |
| 4,432,761 | 2/1984 | Dawe . |
| 4,517,830 | 5/1985 | Gunn et al. . |
| 4,519,239 | 5/1985 | Kiesewetter et al. . |
| 4,554,821 | 11/1985 | Kiesewetter et al. . |
| 4,616,503 | 10/1986 | Plungis et al. . |
| 4,637,250 | 1/1987 | Irvine, Jr. et al. . |
| 4,643,021 | 2/1987 | Mattout . |
| 4,680,957 | 7/1987 | Dodd . |
| 4,680,958 | 7/1987 | Ruelle et al. . |
| 4,750,351 | 6/1988 | Ball . |
| 4,856,322 | 8/1989 | Langrick et al. . |
| 4,858,127 | 8/1989 | Kron et al. . |
| 4,884,577 | 12/1989 | Merrill . |
| 4,899,575 | 2/1990 | Chu et al. . |
| 4,947,678 | 8/1990 | Hori et al. . |
| 5,099,698 | 3/1992 | Kath et al. . |
| 5,142,899 | 9/1992 | Park et al. . |
| 5,181,415 | 1/1993 | Esvan et al. . |
| 5,222,497 | 6/1993 | Ono . |
| 5,224,375 | 7/1993 | You et al. . |
| 5,257,529 | 11/1993 | Taniguchi et al. . |
| 5,271,398 | 12/1993 | Schlain et al. . |
| 5,272,912 | 12/1993 | Katsuzaki . |
| 5,327,778 | 7/1994 | Park . |
| 5,333,497 | 8/1994 | Br nd Dag A et al. . |
| 5,365,776 | 11/1994 | Lehmann et al. . |
| 5,421,328 | 6/1995 | Bedingham . |
| 5,443,078 | 8/1995 | Uflacker . |
| 5,447,440 | 9/1995 | Davis et al. . |
| 5,491,408 | 2/1996 | Rousseau . |
| 5,494,639 | 2/1996 | Grzegorzewski . |
| 5,549,119 | 8/1996 | Solar . |
| 5,686,659 | 11/1997 | Neel et al. . |
| 5,725,563 | 3/1998 | Klotz . |
| B1 3,999,538 | 7/1984 | Philpot, Jr. . |

OTHER PUBLICATIONS

Postprandial changes in plasma and serum viscosity and plasma lipids and lipoproteins after an acute test meal, Tangney, et al. 1997, Amer. J. Clinical Nutrition, 65:36–40.

Studies of Plasma Viscosity in Primary Hyperlipoproteinaemia, Leonhardt, et al., 1977, Atherosclerosis 28, 29–40.

Effects of Lipoproteins on Plasma Viscosity, Seplowitz, et al. 1981, Atherosclerosis 38, 89–95.

Hyperviscosity Syndrome in a Hypercholesterolemic Patient with Primary Biliary Cirrhosis, Rosenson, et al. 1990, Gastroenterology 98: No. 5, 1351–7.

Blood viscosity and risk of cardiovascular events: the Edinburgh Artery Study, Lowe, et al. 1977, British Journal of Haematology 96; 168–173.

Blood Rheology Associated with Cardiovascular Risk Factors and Chronic Cardiovascular Diseases: Results of an Epidemiologic Cross–Sectional Study, Koenig, et al. Nov. 1988, Angiology, J. of Vascular Diseases 986–995.

Importance of Blood Viscoelasticity in Arteriosclerosis, Hell, et al. Jun. '89, Angiology, J. of Vascular Diseases 539–546.

Thermal method for continuous blood velocity measurements in large blood vessels and cardiac–output determination, Delaunois Mar. '73, Med. & Biological Engineering, vol. 11, No. 2, 201–204.

Fluid Mechanics in Atherosclerosis, Nerem, et al 1985, Handbook of Bio–Engineering, Chp. 21.

Theory and Design of Disposable Clinical Blood Viscometer, Litt, et al. 1988, Biorheology, 25: 697–712.

Automated measurement of plasma viscosity by capillary viscometer, Cooke, et al. 1988, J. of Clinical Path. 41: 1213–1216.

A novel computerized viscometer/rheometer, Jimenez/Kostic Jan. '94, Rev. Scientific Instruments, 65:vol. 1.

Measurement of blood viscosity using a conicylindrical viscometer, Walker, et al. Sep. 1976, Medical&Biological Engineering; 551–557.

A New Instrument for the Measurement of Plasma–Viscosity, J. Harkness Aug. 10, 1963, The Lancet, 280–281.

Blood Viscosity and Raynaud's Disease, Pringle, et al. May 22, 1965, The Lancet, 1086–1089.

Measurement of Human Red Blood Cell Deformability Using a Single Micropore on a Thin $Si_3N_4$ Film, Ogura, et al. Aug. '91, IEEE Transactions on Biomedical Engineering, vol. 38 No. 8.

Pall BPF4 High Efficiency Leukocyte Removal Blood Processing Filter System, 1993, Pall Biomedical Products Corporation.

Effects of Whole Blood Viscosity on Atherogenesis, Kensey, et al. Jan./Feb. 1997, Journal of Invasive Cardiology, vol. 9, No. 1.

Cardiovascular Risk Factors and Hemorheology; Physical Fitness, Stress and Obesity, Ernst, et al., Atherosclerosis, vol. 59, 263–269, 1986.

Cigarette Smoking and Hypertension, Levenson, et al. Nov./Dec. 1987, Arteriosclerosis vol. 7, No. 6, 572–577

Blood Viscosity in Human Obesity; Relation to Glucose Tolerance and Insulin Status, Rillaerts, et al., International Journal Of Obesity, vol. 13, 739–741, 1989.

Viscosity and Ischemic Heart Disease, Rosenson, R. Aug. 1993, Journal of Vascular Medicine & Biology, vol. 4, 206–212.

Direct Relationship Between Blood Pressure and Blood Viscosity in Normal and Hypertensive Subjects, Letcher, et al., Am. Journal of Medicine vol. 70, 1195–1202, Jun., 1981.

The Fluid Mechanics of Bonding With Yield Stress Epoxies, Zwick, K. J., Univ. of Pennsylvania, PA USA, 1–142, 1996.

Apparent Viscosity of Whole Human Blood at Various Hydro–static Pressures–I. Studies on Anticoagulated Blood Employing A New Capillary Viscometer, Martin, et al., Biorheology, vol. 11, pp. 3–12, 1978.

Rheologic measurements on small samples with a new capillary viscometer, Reinhart, et al., J. Lab. and Clinical Med. 921–931, Dec. 1984.

A New Capillary Viscometer for Clinical Use, Chmiel, Biorheology, vol. 12, 301–307, 1979.

A Newly Designed Oscillating Viscometer for Blood Viscosity Measurements, Hausler, et al. Biorheology, vol. 33, Nos. 4, 5; 397–404, 1996.

VISCOSITY MEASURING APPARATUS AND METHOD OF USE

RELATED APPLICATIONS

This application is a Divisional application of application Ser. No. 08/919,906, filed Aug. 28, 1997 U.S. Pat. No. 6,019,735, entitled VISCOSITY MEASURING APPARATUS AND METHOD OF USE, assigned to the same Assignee as the present invention and whose entire disclosure is incorporated by reference herein.

BACKGROUND OF THE INVENTION

This invention relates generally to an apparatus and method for measuring the viscosity of liquids, and more particularly, an apparatus and methods for measuring the viscosity of the blood of a living being in-vivo and over a wide range of shears.

The importance of determining the viscosity of blood is well-known. *Fibrogen, Viscosity and White Blood Cell Count Are Major Risk Factors for Ischemic Heart Disease*, by Yarnell et al., Circulation, Vol. 83, No. 3, March 1991; *Postprandial Changes in Plasma and Serum Viscosity and Plasma Lipids and Lipoproteins After an Acute Test Meal*, by Tangney, et al., American Journal for Clinical Nutrition, 65:36–40, 1997; *Studies of Plasma Viscosity in Primary Hyperlipoproteinaemia*, by Leonhardt et al., Atherosclerosis 28, 29–40, 1977; *Effects of Lipoproteins on Plasma Viscosity*, by Seplowitz, et al., Atherosclerosis 38, 89–95, 1981; *Hyperviscosity Syndrome in a Hypercholesterolemic Patient with Primary Biliary Cirrhosis*, Rosenson, et al., Gastroenterology, Vol. 98, No. 5, 1990; *Blood Viscosity and Risk of Cardiovascular Events:the Edinburgh Artery Study*, by Lowe et al., British Journal of Hematology, 96, 168–171, 1997; *Blood Rheology Associated with Cardiovascular Risk Factors and Chronic Cardiovascular Diseases: Results of an Epidemiologic Cross-Sectional Study*, by Koenig, et al., Angiology, The Journal of Vascular Diseases, November 1988; *Importance of Blood Viscoelasticity in Arteriosclerosis*, by Hell, et al., Angiology, The Journal of Vascular Diseases, June, 1989; *Thermal Method for Continuous Blood-Velocity Measurements in Large Blood Vessels, and Cardiac-Output Determination*, by Delanois, Medical and Biological Engineering, Vol. 11, No. 2, March 1973; *Fluid Mechanics in Atherosclerosis*, by Nerem, et al., Handbook of Bioengineering, Chapter 21, 1985.

Much effort has been made to develop apparatus and methods for determining the viscosity of blood. *Theory and Design of Disposable Clinical Blood Viscometer*, by Litt et al., Biorheology, 25, 697–712, 1988; *Automated Measurement of Plasma Viscosity by Capillary Viscometer*, by Cooke, et al., Journal of Clinical Pathology 41, 1213–1216, 1988; *A Novel Computerized Viscometer/Rheometer* by Jimenez and Kostic, Rev. Scientific Instruments 65, Vol 1, January 1994; *A New Instrument for the Measurement of Plasma-Viscosity*, by John Harkness, The Lancet, pp. 280–281, Aug. 10, 1963; *Blood Viscosity and Raynaud's Disease*, by Pringle, et al., The Lancet, pp. 1086–1089, May 22, 1965; *Measurement of Blood Viscosity Using a Conicylindrical Viscometer*, by Walker et al., Medical and Biological Engineering, pp. 551–557, September 1976.

In addition, there are a number of patents relating to blood viscosity measuring apparatus and methods. See for example, U.S. Pat. Nos.: U.S. Pat. No. 3,342,063 (Smythe et al.); U.S. Pat. No. 3,720,097 (Kron); U.S. Pat. No. 3,999,538 (Philpot, Jr.); U.S. Pat. No. 4,083,363 (Philpot); U.S. Pat. No. 4,149,405 (Ringrose); U.S. Pat. No. 4,165,632 (Weber, et. al.); U.S. Pat. No. 4,517,830 (Gunn, deceased, et. al.); U.S. Pat. No. 4,519,239 (Kiesewetter, et. al.); U.S. Pat. No. 4,554,821 (Kiesewetter, et. al.); U.S. Pat. No. 4,858,127 (Kron, et. al.); U.S. Pat. No. 4,884,577 (Merrill); U.S. Pat. No. 4,947,678 (Hori et al.); U.S. Pat. No. 5,181,415 (Esvan et al.); U.S. Pat. No. 5,257,529 (Taniguchi et al.); U.S. Pat. No. 5,271,398 (Schlain et al.); and U.S. Pat. No. 5,447,440 (Davis, et. al.).

The Smythe '063 patent discloses an apparatus for measuring the viscosity of a blood sample based on the pressure detected in a conduit containing the blood sample. The Kron '097 patent discloses a method and apparatus for determining the blood viscosity using a flowmeter, a pressure source and a pressure transducer. The Philpot '538 patent discloses a method of determining blood viscosity by withdrawing blood from the vein at a constant pressure for a predetermined time period and from the volume of blood withdrawn. The Philpot '363 patent discloses an apparatus for determining blood viscosity using a hollow needle, a means for withdrawing and collecting blood from the vein via the hollow needle, a negative pressure measuring device and a timing device. The Ringrose '405 patent discloses a method for measuring the viscosity of blood by placing a sample of it on a support and directing a beam of light through the sample and then detecting the reflected light while vibrating the support at a given frequency and amplitude. The Weber '632 patent discloses a method and apparatus for determining the fluidity of blood by drawing the blood through a capillary tube measuring cell into a reservoir and then returning the blood back through the tube at a constant flow velocity and with the pressure difference between the ends of the capillary tube being directly related to the blood viscosity. The Gunn '830 patent discloses an apparatus for determining blood viscosity that utilizes a transparent hollow tube, a needle at one end, a plunger at the other end for creating a vacuum to extract a predetermined amount and an apertured weight member that is movable within the tube and is movable by gravity at a rate that is a function of the viscosity of the blood. The Kiesewetter '239 patent discloses an apparatus for determining the flow shear stress of suspensions, principally blood, using a measuring chamber comprised of a passage configuration that simulates the natural microcirculation of capillary passages in a being. The Kiesewetter '821 patent discloses another apparatus for determining the viscosity of fluids, particularly blood, that includes the use of two parallel branches of a flow loop in combination with a flow rate measuring device for measuring the flow in one of the branches for determining the blood viscosity. The Kron '127 patent discloses an apparatus and method for determining blood viscosity of a blood sample over a wide range of shear rates. The Merrill '577 patent discloses an apparatus and method for determining the blood viscosity of a blood sample using a hollow column in fluid communication with a chamber containing a porous bed and means for measuring the blood flow rate within the column. The Hori '678 patent discloses a method for measurement of the viscosity change in blood by disposing a temperature sensor in the blood flow and stimulating the blood so as to cause a viscosity change. The Esvan '415 patent discloses an apparatus that detects the change in viscosity of a blood sample based on the relative slip of a drive element and a driven element, which holds the blood sample, that are rotated. The Taniguchi '529 patent discloses a method and apparatus for determining the viscosity of liquids, e.g., a blood sample, utilizing a pair of vertically-aligned tubes coupled together via fine tubes while using a pressure sensor to measure the change of an internal tube pressure with the passage of time and the change of flow rate of the blood. The Bedingham '328 patent discloses an intravascular blood parameter sensing system that uses a catheter and probe having a plurality of sensors (e.g., an $O_2$ sensor, $CO_2$ sensor, etc.) for measuring particular blood parameters in vivo. The Schlain '398 patent discloses a intra-vessel method and apparatus for detecting undesirable wall effect on blood parameter sensors and for moving such sensors to reduce or eliminate the wall effect. The Davis '440 patent discloses an apparatus for conducting a variety of assays that are responsive to a change in the viscosity of a sample fluid, e.g., blood.

Viscosity measuring devices and methods for fluids in general are well-known. See for example, U.S. Pat. Nos.: U.S. Pat. No. 1,810,992 (Dallwitz-Wegner); U.S. Pat. No. 2,343,061 (Irany); U.S. Pat. No. 2,696,734 (Brunstrum et al.); U.S. Pat. No. 2,700,891 (Shafer); U.S. Pat. No. 2,934,944 (Eolkin); U.S. Pat. No. 3,071,961 (Heigl et al.); U.S. Pat. No. 3,116,630 (Piros); U.S. Pat. No. 3,137,161 (Lewis et al.); U.S. Pat. No. 3,138,950 (Welty et al.); U.S. Pat. No. 3,277,694 (Cannon et al.); U.S. Pat. No. 3,286,511 (Harkness); U.S. Pat. No. 3,435,665 (Tzentis); U.S. Pat. No. 3,520,179 (Reed); U.S. Pat. No. 3,604,247 (Gramain et al.); U.S. Pat. No. 3,666,999 (Moreland, Jr. et al.); U.S. Pat. No. 3,680,362 (Geerdes et al.); U.S. Pat. No. 3,699,804 (Gassmann et al.); U.S. Pat. No. 3,713,328 (Aritomi); U.S. Pat. No. 3,782,173 (Van Vessem et al.); U.S. Pat. No. 3,864,962 (Stark et al.); U.S. Pat. No. 3,908,441 (Virloget); U.S. Pat. No. 3,952,577 (Hayes et al.); U.S. Pat. No. 3,990,295 (Renovanz et al.); U.S. Pat. No. 4,149,405 (Ringrose); U.S. Pat. No. 4,302,965 (Johnson et al.); U.S. Pat. No. 4,426,878 (Price et al.); U.S. Pat. No. 4,432,761 (Dawe); U.S. Pat. No. 4,616,503 (Plungis et al.); U.S. Pat. No. 4,637,250 (Irvine, Jr. et al.); U.S. Pat. No. 4,680,957 (Dodd); U.S. Pat. No. 4,680,958 (Ruelle et al.); U.S. Pat. No. 4,750,351 (Ball); U.S. Pat. No. 4,856,322 (Langrick et al.); U.S. Pat. No. 4,899,575 (Chu et al.); U.S. Pat. No. 5,142,899 (Park et al.); U.S. Pat. No. 5,222,497 (Ono); U.S. Pat. No. 5,224,375 (You et al.); 5,257,529 (Taniguchi et al.); U.S. Pat. No. 5,327,778 (Park); and U.S. Pat. No. 5,365,776 (Lehmann et al.).

The following U.S. patents disclose viscosity or flow measuring devices, or liquid level detecting devices using optical monitoring: U.S. Pat. No. 3,908,441 (Virloget); U.S. Pat. No. 5,099,698 (Kath, et. al.); U.S. Pat. No. 5,333,497 (Br nd Dag A. et al.). The Virloget '441 patent discloses a device for use in viscometer that detects the level of a liquid in a transparent tube using photodetection. The Kath '698 patent discloses an apparatus for optically scanning a rotameter flow gauge and determining the position of a float therein. The Br nd Dag A. '497 patent discloses a method and apparatus for continuous measurement of liquid flow velocity of two risers by a charge coupled device (CCD) sensor.

U.S. Pat. No. 5,421,328 (Bedingham) discloses an intravascular blood parameter sensing system.

A statutory invention registration, H93 (Matta et al.) discloses an apparatus and method for measuring elongational viscosity of a test fluid using a movie or video camera to monitor a drop of the fluid under test.

The following publications discuss red blood cell deformability and/or devices used for determining such: *Measurement of Human Red Blood Cell Deformability Using a Single Micropore on a Thin $Si_3N_4$ Film*, by Ogura et al, IEEE Transactions on Biomedical Engineering, Vol. 38, No. 8, August 1991; *the Pall BPF4 High Efficiency Leukocyte Removal Blood Processing Filter System*, Pall Biomedical Products Corporation, 1993.

Notwithstanding the existence of the foregoing technology, a need remains for an apparatus and method for obtaining the viscosity of the blood of a living being in-vivo and over a range of shears and for the provision of such data in a short time span.

OBJECTS OF THE INVENTION

Accordingly, it is the general object of the instant invention to provide an apparatus and methods for meeting that need.

It is a further object of this invention to provide viscosity measuring an apparatus and methods for determining the viscosity of various fluids, e.g., blood over a range of shears.

It is still yet a further object of this invention to provide an apparatus and methods for determining viscosity of a fluid, e.g., the blood of a living being in-vivo without the need to directly measure pressure, flow and volume.

It is yet another object of this invention to provide the viscosity of the blood of a living being in a short span of time.

It is yet another object of this invention to provide an apparatus and methods for measuring the viscosity of the blood of a living being in-vivo and with minimum invasiveness.

It is still yet another object of the present invention to provide an apparatus and methods for measuring the viscosity of the blood of a living being that does not require the use of anti-coagulants, or other chemicals or biologically active materials.

It is still yet another object of the present invention to provide an apparatus and methods measuring the blood viscosity of a living being in-vivo that comprises disposable portions for maintaining a sterile environment, ease of use and repeat testing.

It is still yet another object of the present invention to provide a blood viscosity measuring apparatus and methods for determining the thixotropic point of the blood.

It is still even a further object of the present invention to provide a viscosity measuring apparatus and method that can be used to determine the viscosity of other materials.

It is still a further object of this invention to provide an apparatus and methods for determining the effect of vibratory energy on blood viscosity of a living being.

It is still a further object of this invention to provide apparatus and methods for applying vibratory energy to the body of a living being to affect a beneficial change in the person's blood viscosity.

SUMMARY OF THE INVENTION

These and other objects of this invention are achieved by providing apparatus and methods for effecting the in-vivo measurement of the viscosity of the blood (or of blood plasma) of a living being, or for effecting the measurement of the viscosity of other non-newtonian fluids, cosmetics, oil, grease, etc, at plural shear rates.

In accordance with one aspect of the invention the apparatus comprises blood sampling means and calculation means. The blood sampling means, e.g., a capillary tube of predetermined internal diameter and predetermined length, at least a portion of which is arranged to be located in the body of the being, e.g., placed intravenously, for exposure to the being's blood, e.g., for blood to flow therethrough. The calculation means, e.g., a riser tube having a column of liquid therein, an associated CCD sensor, and microprocessor, is coupled to the blood sampling means. The calculation means is arranged to determine the viscosity of the being's blood at plural shear rates.

For example, in one exemplary aspect of the invention the apparatus is used to determine the being's blood viscosity by selectively positioning the blood sampling means, e.g., the capillary tube, with respect to the calculation means, e.g., the riser tube, and selectively coupling the flow of blood therebetween, e.g., selectively enabling blood to flow through the capillary tube and coupling that flow to the liquid column in the riser tube, to cause that column of fluid to change in height under the influence of gravity. The calculation means, e.g., the CCD sensor and associated microprocessor, monitors the changing height of the column of fluid at plural points along at least a portion of the length of the riser tube and calculates the viscosity of the blood in accordance with a predetermined algorithm.

In accordance with another aspect of this invention vibratory energy, e.g., energy which is adjustable in amplitude and/or frequency, is applied to a portion of the body of the being before and/or during the determination of the being's blood viscosity to provide information regarding the effect of such vibratory energy on the blood's viscosity. This information can be used to provide therapy vibratory energy to be being's body to alter the being's blood viscosity in the interests of improving blood circulation.

DESCRIPTION OF THE DRAWINGS

Other objects and many of the intended advantages of this invention will be readily appreciated when the same becomes better understood by reference to the following detailed description when considered in connection with the accompanying drawings wherein.

DETAILED DESCRIPTION OF THE PREFERRED EMBODIMENTS

This application incorporates by reference the entire disclosure of U.S. application Ser. No. 08/919,906, filed on Aug. 28, 1997.

Figure 1A:
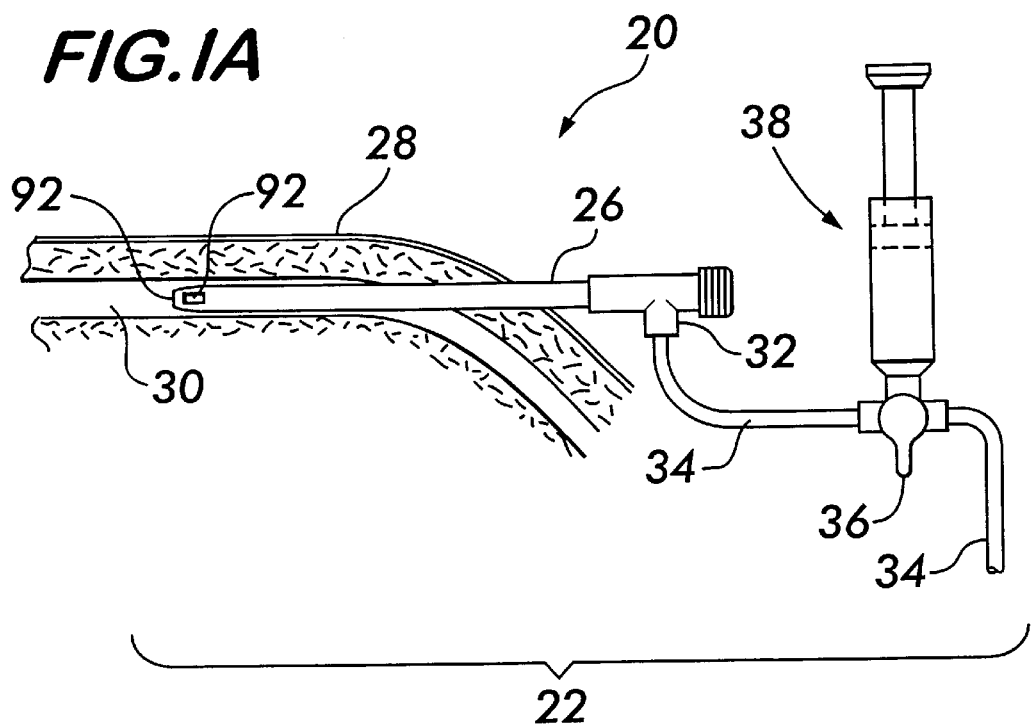
FIGS. 1A and 1B form an illustration and functional diagram of one embodiment of a system for in-vivo measuring the viscosity of the blood of a human being.
Figure 1B:
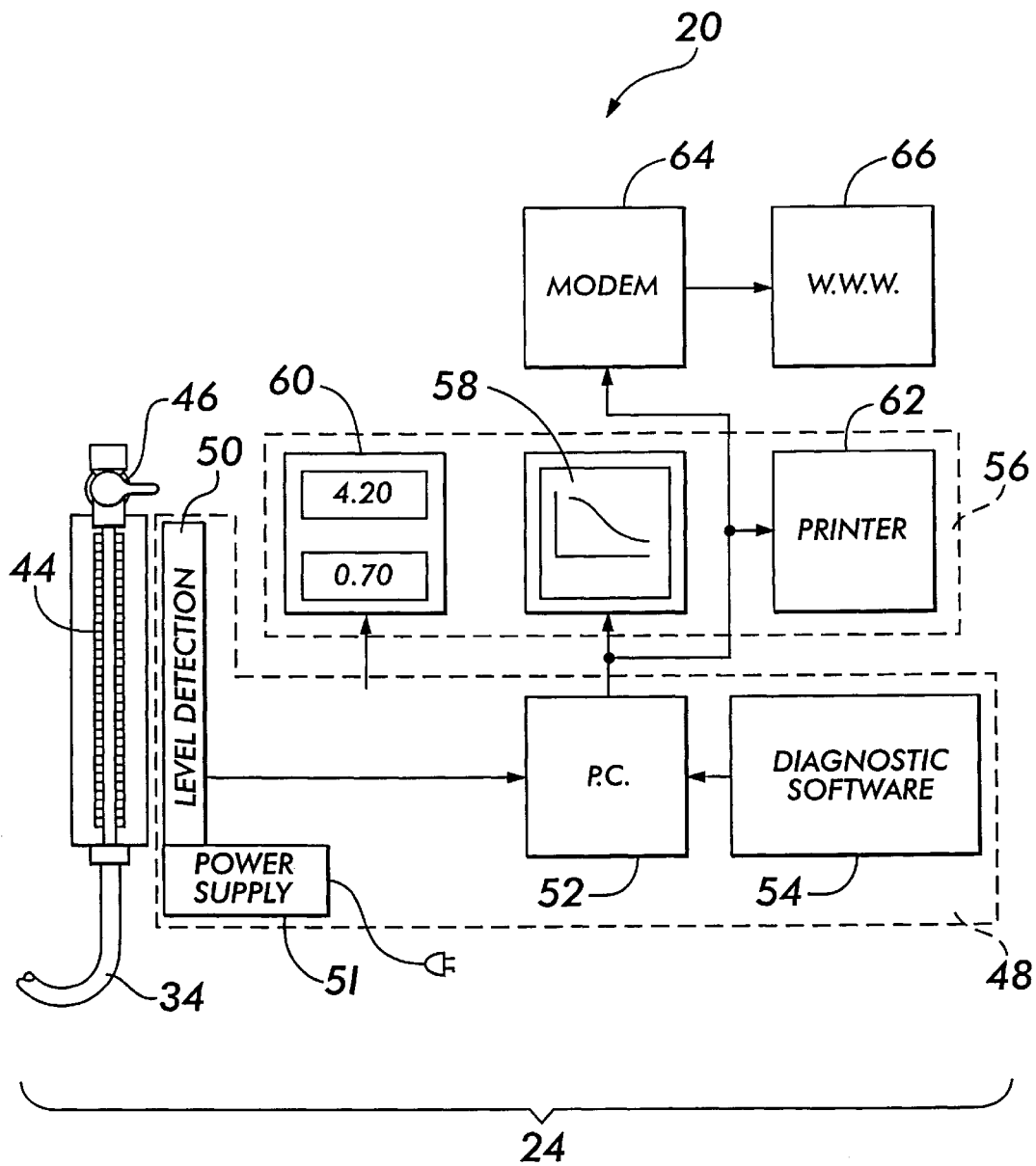

Referring now in greater detail to the various figures of the drawing, wherein like reference characters refer to like parts, there is shown in FIGS. 1A and 1B at 20 a liquid viscosity measuring system constructed in accordance with the present invention. The system 20 has particular utility for measuring in-vivo the viscosity of the blood of a living being.

Although the apparatus 20 has many applications, the preferred embodiment of the apparatus 20 is used to measure the viscosity of the blood anywhere in a patient's vascular system, e.g., veins, arteries, pulmonary system, left atrium, left ventricle, etc.

It should be understood that blood is a non-Newtonian fluid. A Newtonian fluid may be defined as one in which the viscosity does not vary with the rate of shear within the non-turbulent flow range, whereas a non-Newtonian fluid, such as blood, exhibits a viscosity that is variable with the rate of shear in the non-turbulent flow range. As a result, when the viscosity of a non-Newtonian fluid is plotted as a function of rate of shear, a curve is produced, instead of a straight line. Therefore, to obtain an accurate determination of blood viscosity, it is necessary to obtain a viscosity measurement over a range of shears.

The concept of the present invention is to monitor, on a substantially continuous basis, the rising head of an externally located column of fluid coupled to a portion of the patient's body in which the blood flows, thus, effectively monitoring the patient's blood in-vivo. The data from this rising head is used to calculate the viscosity of the blood at a large multiplicity of points during the rise of the column for various different flow rates, thereby providing a viscosity of the blood over a range of shears. The monitoring of the rising column solves the problem of how to generate a range of shears necessary to obtain an accurate measurement of the blood viscosity.

As shown in FIGS. 1A and 1B, the apparatus 20 basically comprises a blood sampling means 22 and a calculation means 24 that are coupled together to provide the viscosity measurement. The blood sampling means 22 comprises a catheter 26, which in a preferred embodiment comprises a capillary tube. The catheter 26 has an inside diameter $D_1$ and a length, $L_1$. The catheter 26 is introduced into the body 28 of the being (patient) to an internal situs 30 (e.g., a vein, artery, etc.) to enable blood 31 to flow into the catheter 26. Thus, the catheter 26 serves as a blood receiving means. The catheter 26 is connected via a hub 32 to a conduit means 34 having a inside diameter $D_2$. A first valve means 36 (e.g., a 3-way valve) selectively couples an injector means 38 to the conduit means 34. The injector means 38 comprises a reservoir 40 for containing an indicator or transmission fluid 41 (e.g., a liquid such as saline solution, alcohol, or any sterile water-type liquid) which, when injected into the conduit means 34, forms a column of fluid 42 (to be discussed later) that can be monitored (e.g., optically monitored-an optimum dye can be used for coloring the transmission fluid for maximizing readability by an optical sensor). The other end of the conduit means 34 is coupled to a riser tube 44. The hollow interior of the riser tube 44 forms a lumen that permits the column of fluid 42 level to be detected as a function of time. The riser tube 44 has an inside diameter of $D_3$. The upper end of the riser tube 44 comprises a second valve means 46 (e.g., a 2-way valve) that vents the riser tube 44 to atmosphere when the valve 46 is opened. The first valve means 36 and second valve means 46 preferably include hydrophobic vents (not shown) to eliminate blood spillage.

It should be understood that optimum selection of the tube sizes for the capillary tube 26, the conduit means 34 and the riser tube 44 minimizes the effects of viscosity and surface tension of the transmission fluid 41. It should also be understood that it is preferable to have the capillary tube 26 fully inserted into the vascular system, i.e., the capillary tube 26 is inserted such that a continuation of the conduit means 34 of diameter $D_2$ is also disposed in the vascular system.

The column of fluid 42 is monitored by monitoring means 48. The monitoring means 48 comprises a sensor means 50 (e.g., a charge-coupled device, CCD, including associated electronics, FIG. 11 and an associated power supply 51) coupled to a microprocessor means 52 (e.g., a personal computer) which further comprises appropriate diagnostic software 54. The monitoring means 48 monitors the height of the column of fluid 42 as it rises throughout the length of the riser tube 44 during the test or run to determine the patient's blood viscosity.

Peripheral indicator means 56, e.g., a visual display 58, a counter means 60, a printer 62, provides data and/or graphics pertaining to the viscosity/shear rate measurements. In addition, a modem 64 can be connected to the monitoring means 48 to provide all pertinent data to some remote location, e.g., via the Internet or World Wide Web 66.

In accordance with a preferred aspect of this invention, the visual display 58 and/or printer 62 serve to present graphical representations of measured parameters such as viscosity vs. shear, or viscosity vs. height of column of fluid ("head"), or diagnoses. The counter means 60 is used to numerically display such items as viscosity at a particular shear and/or the head at which the velocity of the column of fluid is zero, e.g., the thixotropic point (to be discussed later). The viscosity/shear rate data can be stored in the microprocessor means 52 and can be compared with databases 54 (on associated CD-ROM, diskette or PC cards) to present possible diagnoses to the physician.

Figure 2A:
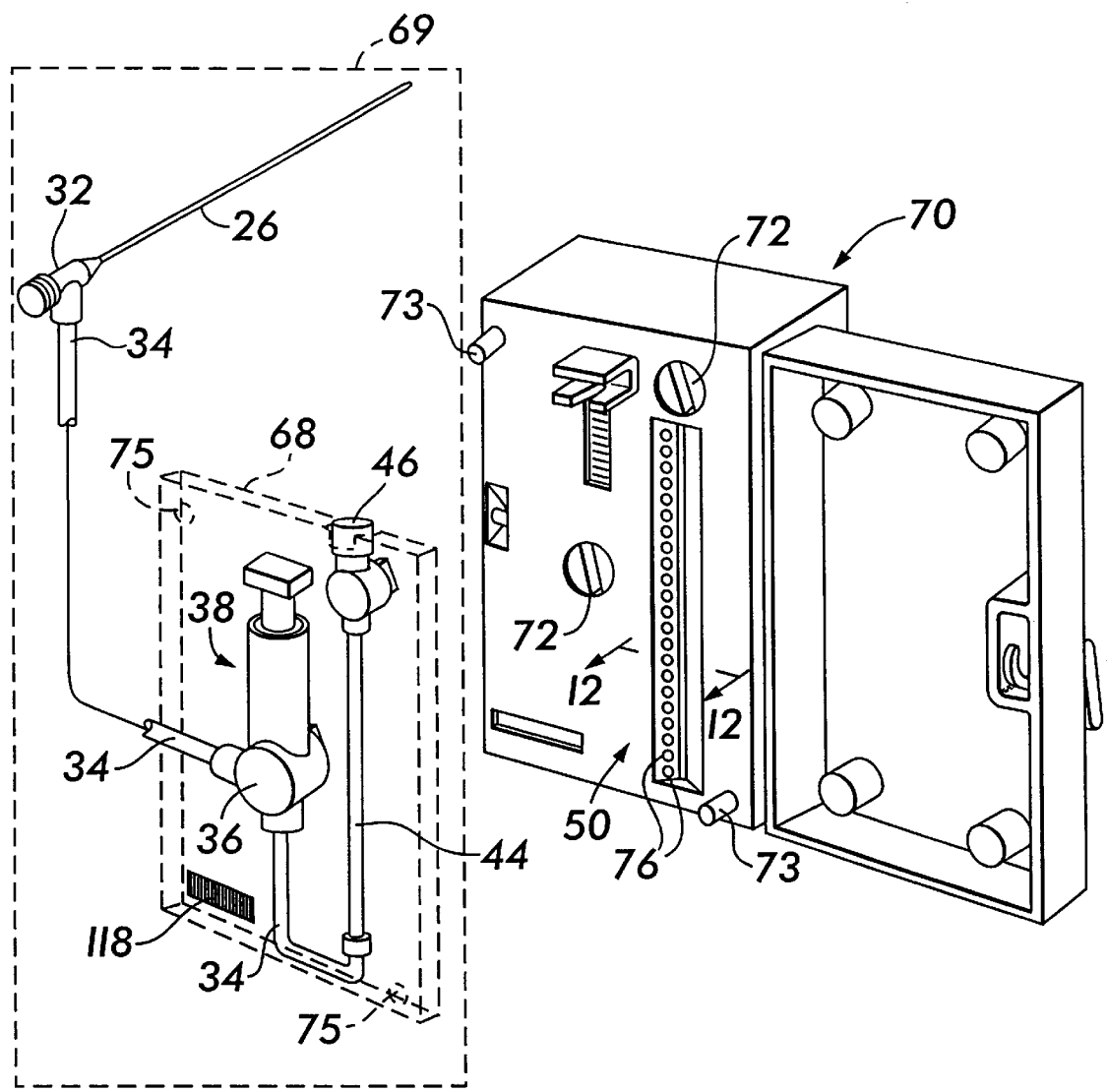
FIG. 2A is an isometric view of a portion of the system shown in FIG. 1, namely, a portion of blood receiving means and monitoring means.

FIG. 2A depicts one portion of the implementation of the system 20. As shown, the injector means 38, a portion of the conduit means 34, the first valve means 36, the riser 44, and the second valve means 46 are mounted on a support plate 68 to form a tubing assembly 69. The tubing assembly 69 is configured to be removably mounted inside a housing 70 which contains the sensor means 50 and the power supply 51. The support plate 68 is mounted in the housing 70 with the appropriate connections in order to position the riser tube 44 vertically and directly opposite the sensor means 50 for proper monitoring. In addition, during insertion of the tubing assembly 69, the appropriate valve control connections 72 are made so that the first valve means 36 and second valve means 46 can be properly controlled automatically in sequence. Location pins 73 and location holes 75 are provided to ensure that the support plate 68 is properly aligned, thereby disposing the riser tube 44 directly opposite the sensor means 50. The support plate 68 comprises a transparent material that permits the sensor means 50 to optically monitor the column of fluid 42. It should be understood that the injector means 38 is pre-charged with the transmission fluid 41 which is held captive in the reservoir 40 by the 3-way valve 36. Only when the valve 36 is properly oriented, does the transmission fluid 41 flow out of the injector means 38 and into the conduit means 34.

Once the tubing assembly 69 is secured in the housing 70, a door 74 can be releasably secured to create a sufficiently dark environment to support proper column illumination 76 and level detection by the sensor means 50 during the run. Once a viscosity measurement procedure or run is completed, the tubing assembly 69 is removed, disconnected from the capillary tube 26, and then discarded. To run another test, a new tubing assembly 69 is connected to the capillary tube 26 and re-installed into the housing 70.

It should be understood that it is within the broadest scope of this invention that the first 36 and second valve means 46 can be controlled manually, i.e., proper operation of the apparatus 20 does not require automatic control of the first 36 and second valve means 46.

Figure 2B:
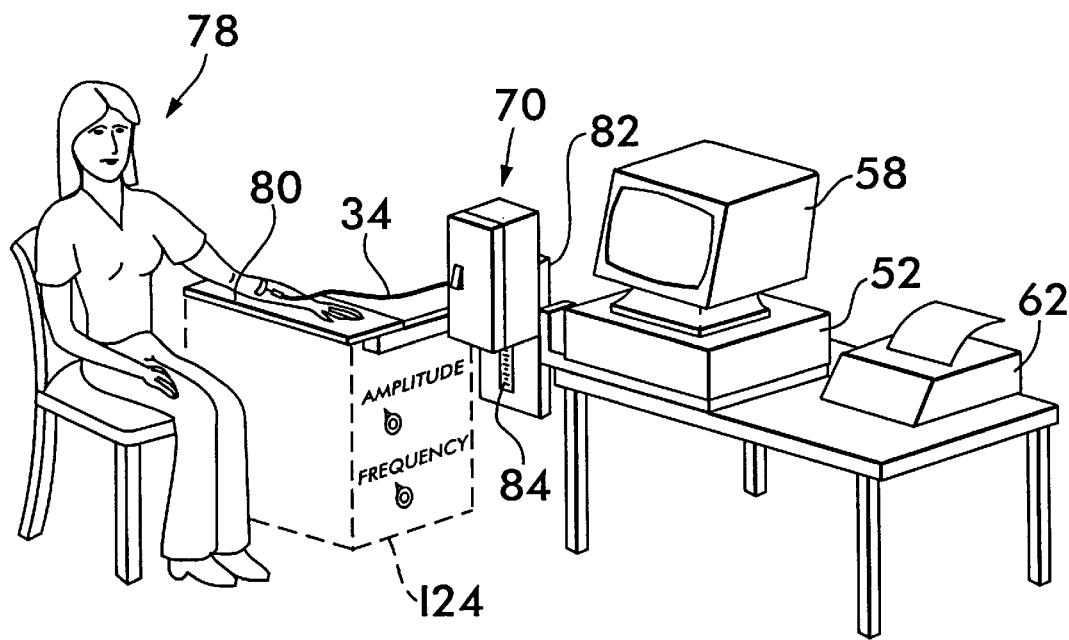
FIG. 2B is an isometric view of another portion of the system shown in FIG. 1, namely, an exemplary test station.

An exemplary test station is shown in FIG. 2B. It should be understood that although the apparatus 20 is shown with the capillary 26 inserted into a patient's arm, the apparatus 20 is not limited in use with that portion of the patient's body. Other station configurations could be used where the capillary 26 is inserted into other portions of the patient's body for blood to flow into the capillary tube 26. With the test station shown in FIG. 2B, the patient 78 is seated with his/her arm disposed on a horizontal surface 80. The capillary 26 is inserted percutaneously into the patient's arm until its distal end, and preferably its entire length $L_1$, is within a desired vessel, e.g., a vein. The conduit means 34 couples the capillary 26 to the housing 70. The housing 70 is releasably disposed on a fixed vertical surface 82. The vertical surface 82 comprises adjustment means 84 that permit the entire housing 70 to be manually displaced in a vertical direction and then releasably secured at any desired vertical height. The important point is that the operator can change the relative vertical position of the housing 70 with respect to the vertical position of the portion of the patient in which the capillary tube 26 has been inserted for reasons to be understood later. The microprocessor means 52, visual display 58 and printer 62 are also shown at the station.

Figure 3:
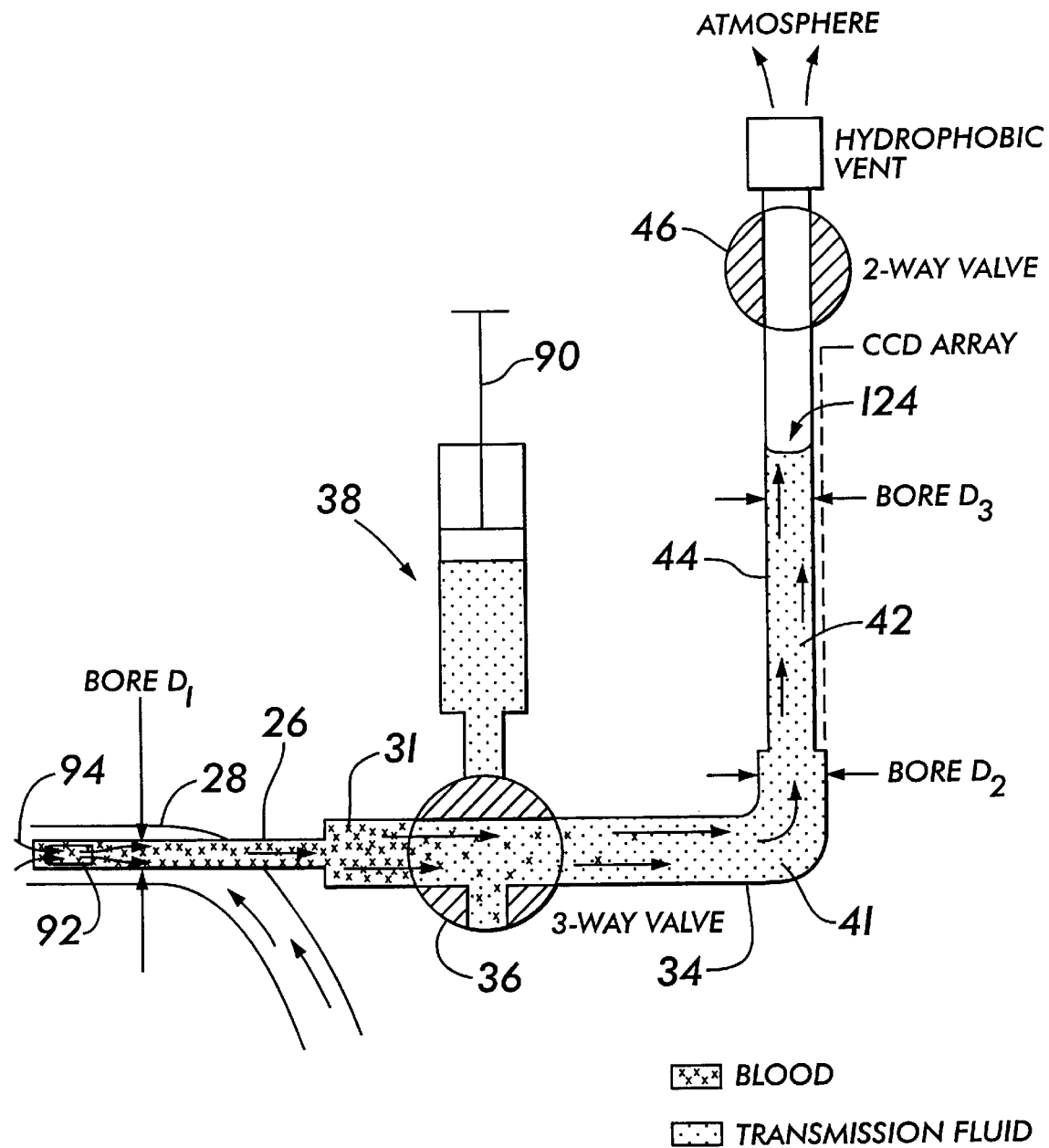
FIG. 3 is an illustration of the construction and function of the blood receiving means.

FIG. 3 is a functional diagram of the apparatus 20. With respect to FIG. 3, the basic operation of the apparatus 20 is shown in FIG. 3. As blood 31 flows into and through the capillary tube 26 and into the conduit means 34, the blood 31 encounters the transmission fluid 41 and displaces the transmission fluid 41 up into the riser tube 44, thereby forming the column of fluid 42. The sensor means 50 (e.g., a CCD array) monitors the rise of the column of fluid 42 in real time by detecting the interface between the top of the column of transmission fluid 42 and the gas (e.g., air) in the riser tube above the fluid. This optical interface (e.g., meniscus) is readily detectable by the sensor means 50. Operation of the first valve means 36 and second valve means 46 are discussed below.

If the following assumptions are made, in particular, $D_1$ is much less than $D_2$;

and $D_1$ is much less than $D_3$ then it can be shown that the viscosity ($\eta_1(t)$) and the shear ($\dot{\gamma}_1(t)$) of the blood in the capillary tube 26 are given by:

$$\eta_1(t) = \left(\frac{\rho_s g t D_1^4}{32 L_1 D_3^2}\right) \cdot \frac{1}{\ln\left(\frac{h_\infty}{h_\infty - h(t)}\right)}$$

$$\dot{\gamma}_1(t) = \frac{8 D_3^2}{D_1^3}\left(h_\infty \left(\frac{\rho_s g}{A}\right) e^{-\frac{\rho_s g t}{A}}\right),$$

$$\text{where} \quad A = 32\eta_1(t) L_1 \frac{D_3^2}{D_1^4}$$

where $\eta_1(t)$ represents the viscosity;

$\dot{\gamma}_1(t)$ represents the shear rate;

$\rho_s$ represents the density of the transmission or indicator fluid;

g represents the gravitational constant;

t represents the time of measurement, $D_1$ represents the inside diameter of the capillary tube;

$L_1$ represents the length of the capillary tube;

$D_3$ represents the inside diameter of the column of transmission or indicator fluid;

$h_\infty$ represents the final height of the column of transmission or indicator fluid; and h(t) represents the instantaneous height of the column of transmission or indicator fluid.

Figure 4:
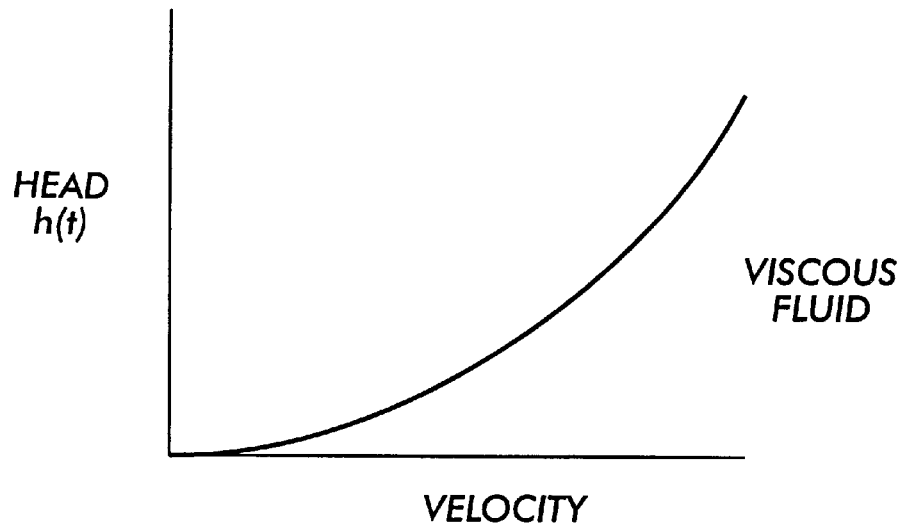
FIG. 4 is a graph of a parameter measured by the system if FIG. 1, namely, the "head" of the column of fluid plotted versus time.

The viscosity, $\eta_1(t)$, of the blood is thus graphically represented as shown in FIG. 4. To increase the range of shears, a longer capillary tube 26 can be used (i.e., increase $L_1$).

Operation of the apparatus 20 is depicted in FIGS. 5A–5H and is as follows:

The portion of the patient's vascular system (e.g., vein, artery, etc.) into which the capillary tube 26 is to be inserted is disposed on the horizontal surface 80. This entry point on the patient becomes the "DATUM" reference and it represents a vertical height reference.

Figure 5A:
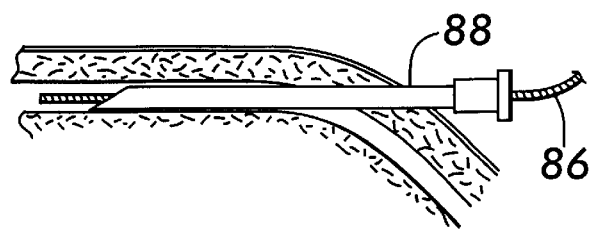
FIGS. 5A–5G are illustrations of a portion of the system shown in FIG. 1 showing the operational sequence thereof.
Figure 5B:
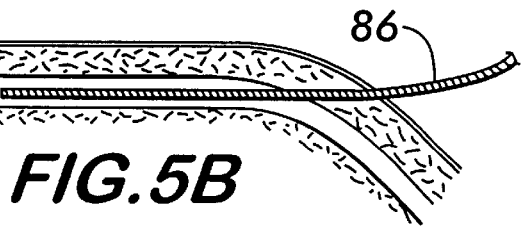

FIGS. 5A–5B: A guidewire 86 is introduced into the vascular system of the patient via a piercer 88. The piercer 88 is removed, leaving the guidewire 86 in place.

Figure 5C:
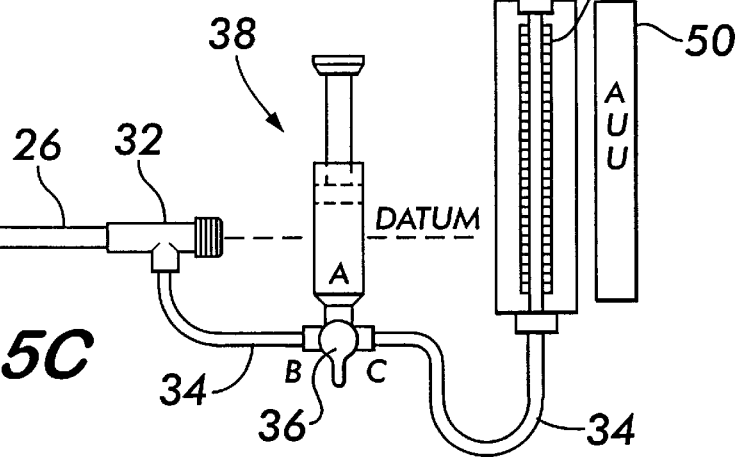

The following steps are preferably automated so that once the capillary tube 26 is inserted in the patient, the operator need only activate a switch (not shown) of a controller (also not shown) that would automatically carry out the following steps:

FIG. 5C: First valve means 36 is opened so that ports A and B are in communication while ports A to C and B to C are closed; the second valve means 46 is closed. The capillary 26 is then flushed.

Figure 5D:
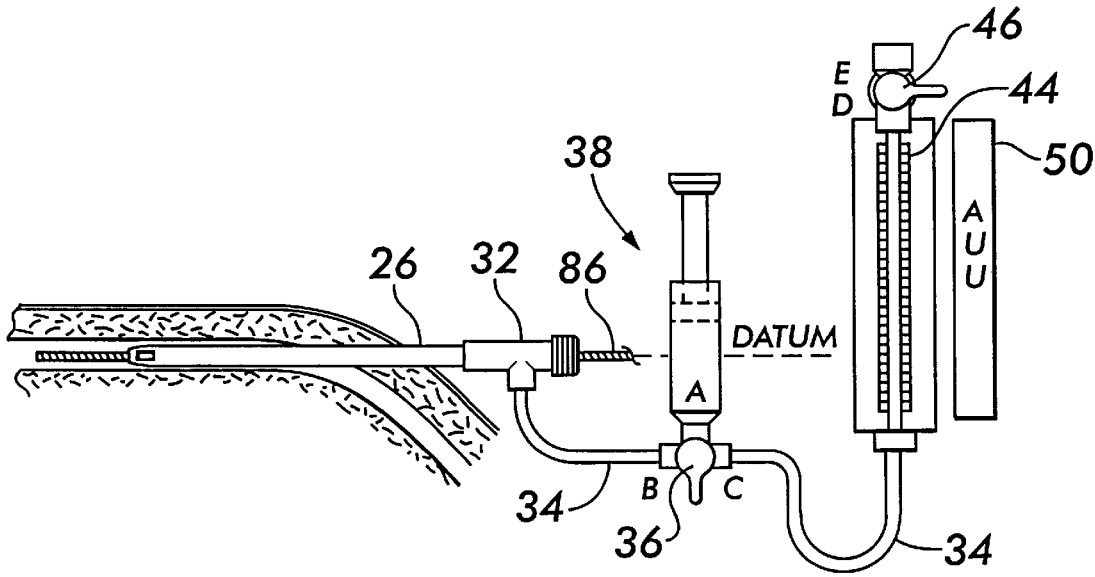

FIG. 5D: First valve means 36 is totally closed and the capillary 26 is threaded over the guidewire 86 and then disposed into the patient's vascular system. The DATUM level is established for the capillary tube 26 and the riser tube 44. A DATUM mark is made on the fixed vertical surface 82.

Figure 5E:
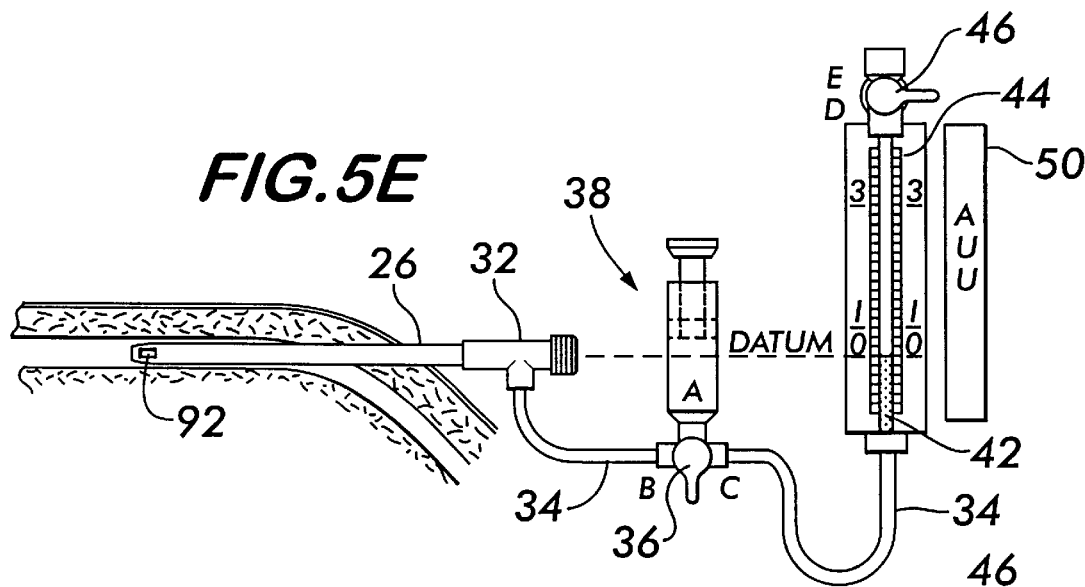

FIG. 5E: The guidewire 86 is removed and the DATUM level is established for the capillary tube 26 and the riser tube 44. A "0" mark is created on the riser tube 44 that is aligned with the DATUM level.

Figure 5F:
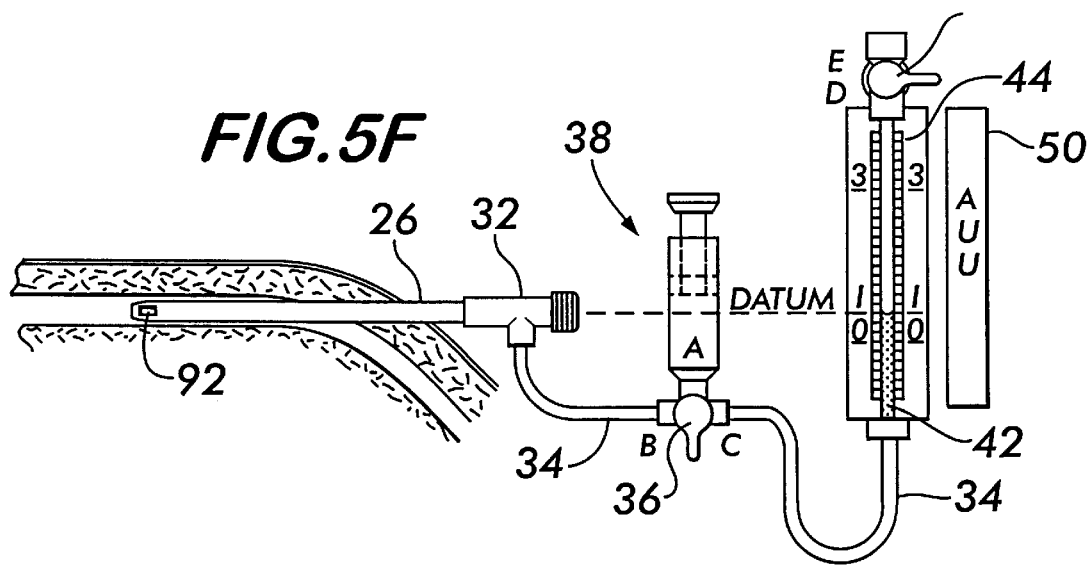

FIG. 5F: First valve means 36 is moved to open communication between ports A and C and second valve means 46 is moved to open communication between ports D and E. The operator then depresses the plunger 90 on the injection means 38 to fill the riser tube 44 with transmission or indicator fluid up to the "0" or DATUM mark. Both the first valve means 36 and the second valve means 46 are then closed.

FIG. 5F: Permit blood pressure to pressurize the column of fluid 42. The operator opens the first valve means 36 so that ports B and C are in communication, thereby permitting blood to flow (approximately 0.5 cc of blood) into conduit means 34. The column of fluid 42 will rise from the 0 mark to a new level. The operator then manually displaces the housing 70 downward until the new level is aligned with the DATUM mark on the fixed vertical surface 82. This action permits the determination of blood's (e.g., the venous) static pressure using the closed-off riser tube 44 as a "barometer."

Figure 5G:
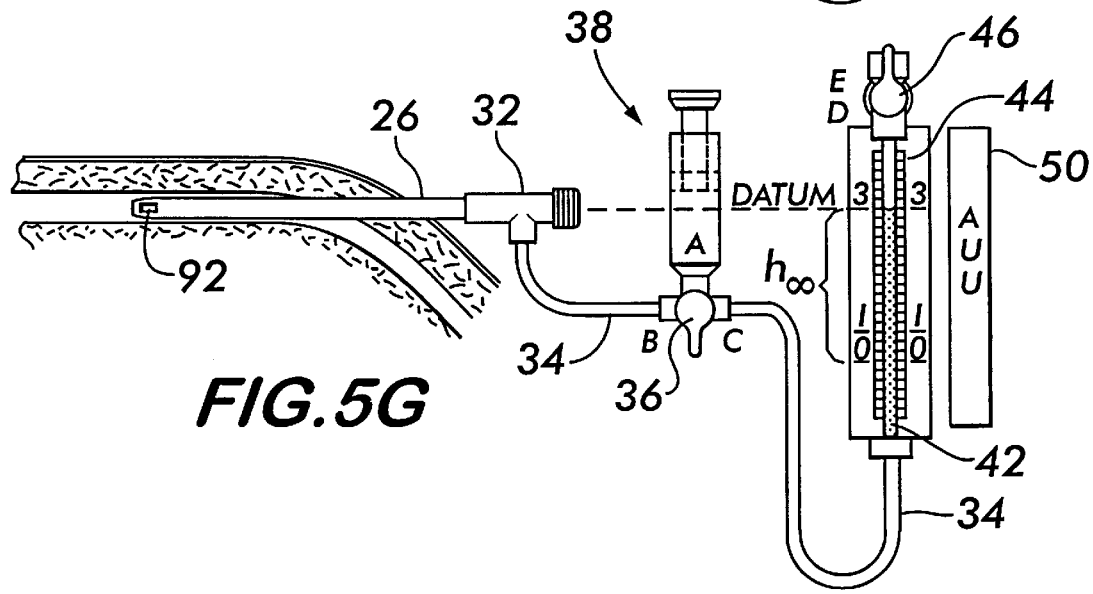

FIG. 5G: To avoid overflowing the riser tube 44 during the run, it is necessary to calculate the approximate final level or head, $h_\infty$, of the column of fluid 42 and to lower the housing 70 by that amount. Boyle's Law is used to estimate the likely rise $h_\infty$ of the column of fluid 42 in step 5F. The housing 70 is then dropped by the amount $h_\infty$. The housing 70 is then secured at that height to prepare the sensor means 50 to monitor the rise of the column of fluid 42. The second valve means 46 is then opened and the column of fluid 42 begins to rise.

If the test is to be run again, the tubing assembly 69 is discarded and a new tubing assembly 69 installed in the housing. If the transmission fluid 41 in the injector means 38 is of a biocompatible material, a portion of the transmission fluid 41 can be used to flush the apparatus 20, all the way to the tip of the capillary tube 26, as shown in FIG. 5C.

Before a viscosity measuring run is made and as part of the automated procedure discussed above, a current barometric pressure reading is obtained (e.g., from a barometer not shown, internal to the calculation means 24) and is provided to the microprocessor means 52. Thus, the apparatus 20 calculates the proper viscosity/shear rate plot based on the existing current atmospheric pressure. In addition, vents may be provided throughout the apparatus 20 to minimize the effect on computed viscosity accuracy.

It should be understood that the process described above could also be accomplished with the use of a hemostasis valve (e.g., a "Heparin Lock") between the capillary tube 26 and the conduit means 34. This allows the capillary tube 26 to be left in place when a plurality of runs are to be made. Furthermore, a hemostasis valve having a "Y" fitting could be disposed close to the point where the capillary tube 28 enters the vessel in order to permit the passage of a the guide wire 86 after the apparatus 20 is flushed without getting air bubbles.

Figure 6:
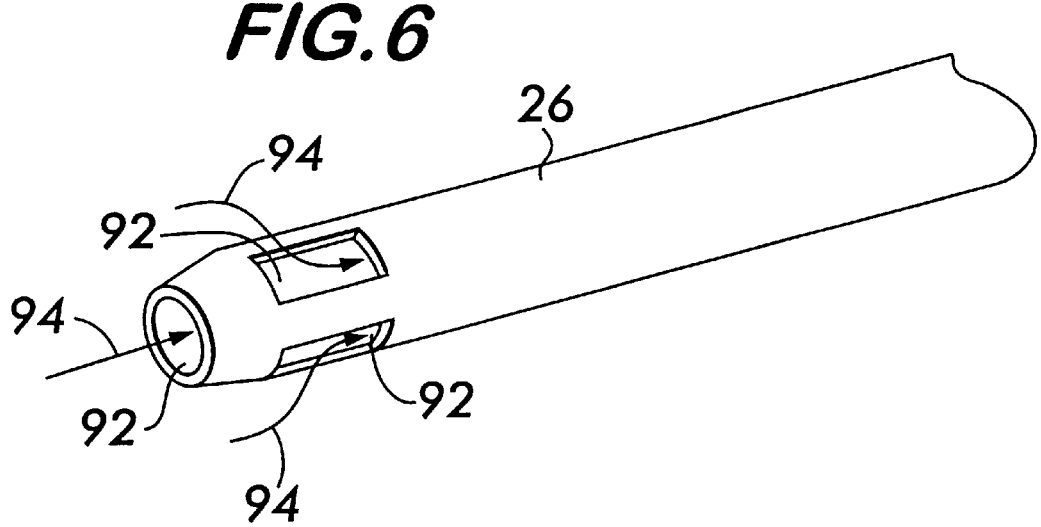
FIG. 6 is an enlarged isometric view of a portion of the system, namely, a capillary tube.

The capillary tube 26 should constructed of, or coated with, a material or materials that prevent the blood 31 from adhering to the capillary tube's internal walls, e.g., an anti-thrombogenic material, such as Heparin, and/or anti-thrombolytic coatings, e.g., phosphoryl choline, etc., can be used to minimize blood clotting. Phosphoryl choline compounds are available from Biocompatibles, Ltd., Uxbridge, UK. Such a construction or coatings facilitate the long-term placement of the capillary tube 26 within the vascular system of the patient. Furthermore, as shown most clearly in FIG. 6, the tip of the capillary tube 26 preferably comprises a plurality of ports 92. This ensures that if the tip of the capillary tube 26 abuts any portion of the interior of the vessel wall once inserted into the patient's vascular system, blood flow entry 94 into the capillary tube 26 will not be obstructed or impeded.

Figure 7:
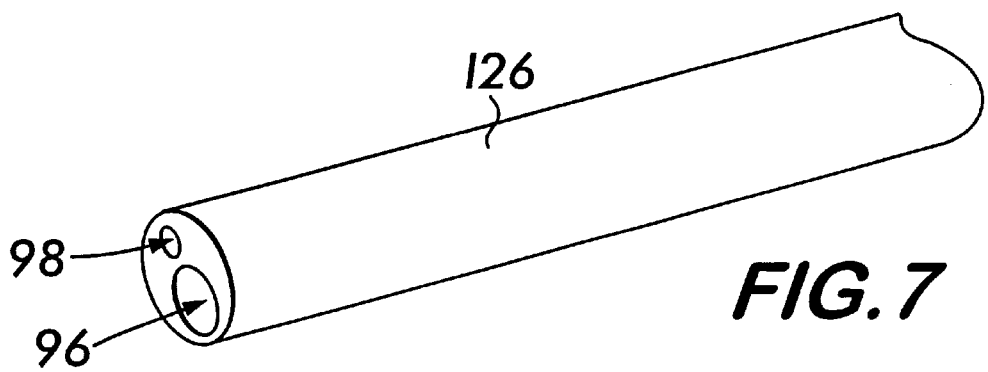
FIG. 7 is a view similar to FIG. 6, but showing an alternative embodiment of the capillary tube.

An alternative embodiment of the capillary tube 26 is shown in FIG. 7 and includes an intravascular capillary with a controlled lumen or resistor for the viscometer function and with another for measuring pressure. For example, the capillary tube 126 comprises a first lumen 96 for transmitting the blood 31 as discussed previously and comprises a second lumen 98 that is coupled to a pressure transducer (not shown) that is coupled to the calculation means 24. Thus, the second lumen 98 provides a continuous reference of the patient's blood pressure to the calculation means 24. Unlike the process described earlier, whereby the operator determines the patient's blood pressure before the test is run, using this second lumen 98, the calculation means 24 is provided with a continuous blood pressure reference throughout the run. In some patients, the actual blood pressure may change during the run. Such blood pressure variations or pulsations need to be accounted for in determining the proper viscosity/shear versus time curve. Having a continuous blood pressure reference can thus be compensated for during the blood viscosity/shear determination.

Figure 8A:
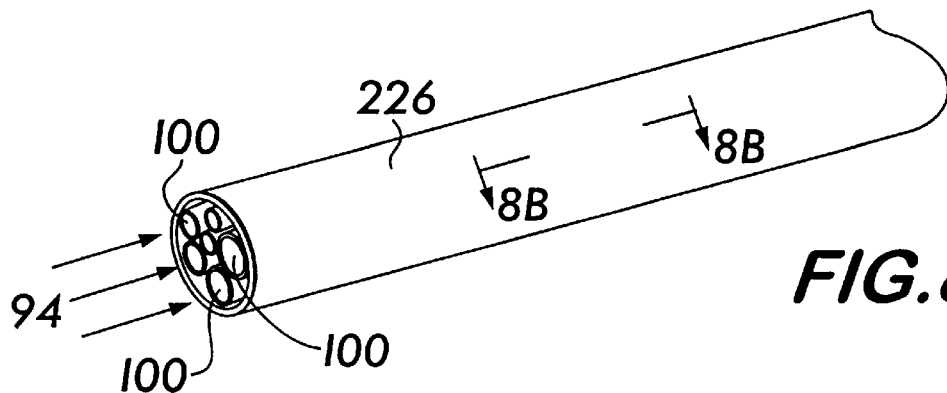
FIG. 8A is a view similar to FIGS. 6 and 7, but showing an alternative embodiment of the capillary tube.
Figure 8B:
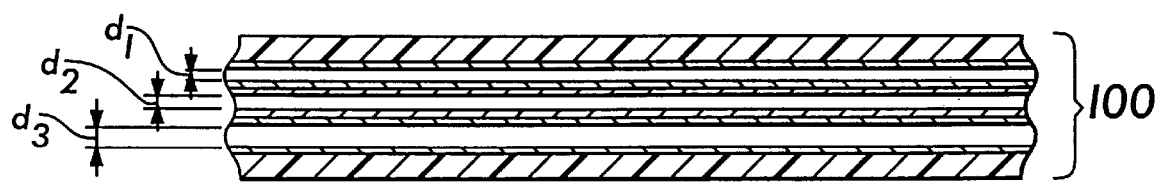
FIG. 8B is a greatly enlarged cross-sectional view taken along line 8B—8B of FIG. 8A.
Figure 9:
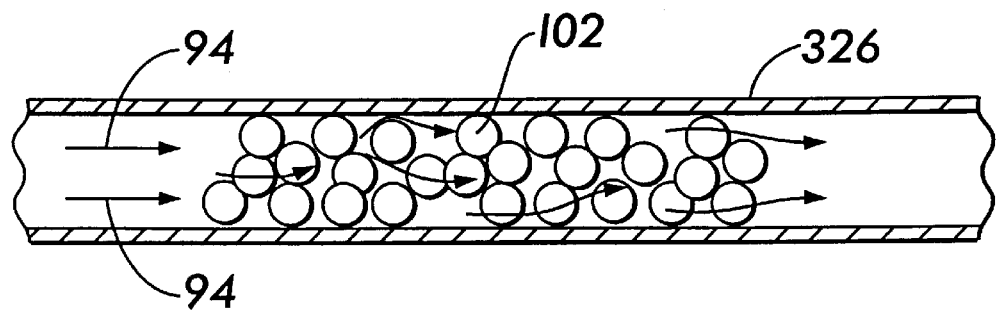
FIG. 9 is an enlarged cross-sectional view of yet another alternative embodiment of the capillary tube.

Another alternative embodiment of the capillary tube 26 is shown in FIGS. 8A–8B and 9. This embodiment includes an intravascular capillary with a controlled lumen or tube with alternative resistive members, such as a number of small capillary tubes in a bundle (FIGS. 8A–8B). Alternatively, the tube is filled with very small spheres (FIG. 9), or a sintered column (not shown). With respect to the embodiment as shown in FIGS. 8A–8B, the capillary tube 226 comprises a plurality of small capillaries 100, each having different internal diameters ($d_1$, $d_2$, $d_3$, etc.). Use of the plurality of small capillaries not only permits the length $L_1$ to be smaller but also permits the attainment of very small shears. Where these diameters are less than the average diameters of a typical red blood cell, the system 20 can be used to determine the blood pressure at which blood flow starts. This action provides an indication of the deformability of the being's red blood cells since those cells will have to deform to pass through the small capillaries 100.

In the alternative embodiment of the capillary tube shown in FIG. 9, the capillary tube 326 includes very small spheres 102 within it to create interstices which are smaller than the average diameter of a red blood cell, so that such cells will have to deform to pass therethrough.

Figure 10:
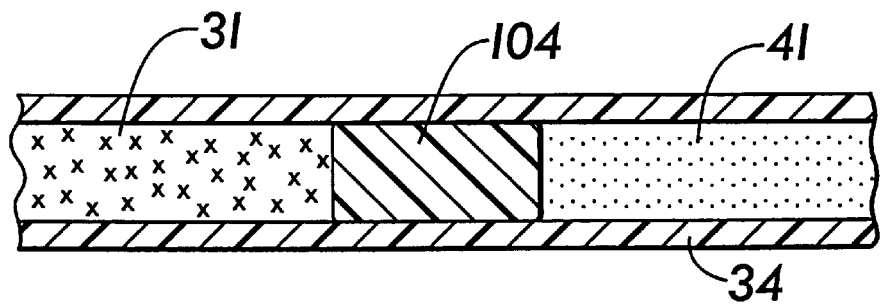
FIG. 10 is an enlarged sectional view through a portion of the components shown in FIG. 3 to include means, e.g., a buffer piston at the blood/transmission fluid interface to isolate the blood of the being from the transmission fluid used by the system.

To eliminate or at least minimize the possible miscibility/contamination problem between the transmission fluid/blood interface in the conduit means 34, a buffer piston as shown in FIG. 10 may be used. That piston can be of any suitable construction, e.g., a carbon slug to isolate the blood 31 from the transmission fluid 41 at their interface. In particular, the piston 104, having a specific gravity of approximately 1.0, transmits the motion or flow of the blood 31 down the capillary tube to the transmission fluid 41 while isolating or separating these two fluids from each other. Alternatively, although not shown, a buffer fluid could be introduced at the interface between the blood 31 and the transmission fluid 41 to reduce any miscibility/contamination problems.

Figure 12:
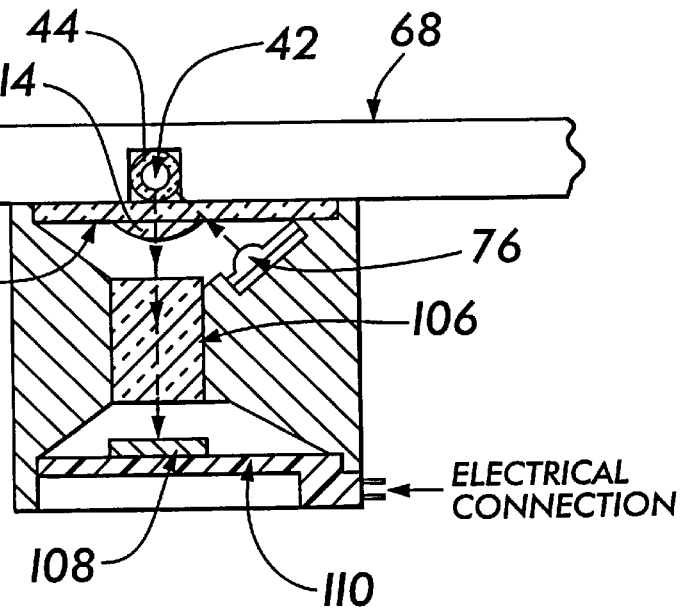
FIG. 12 is an enlarged cross-sectional view of the sensor means taken along line 12—12 of FIG. 2A.
Figure 11:
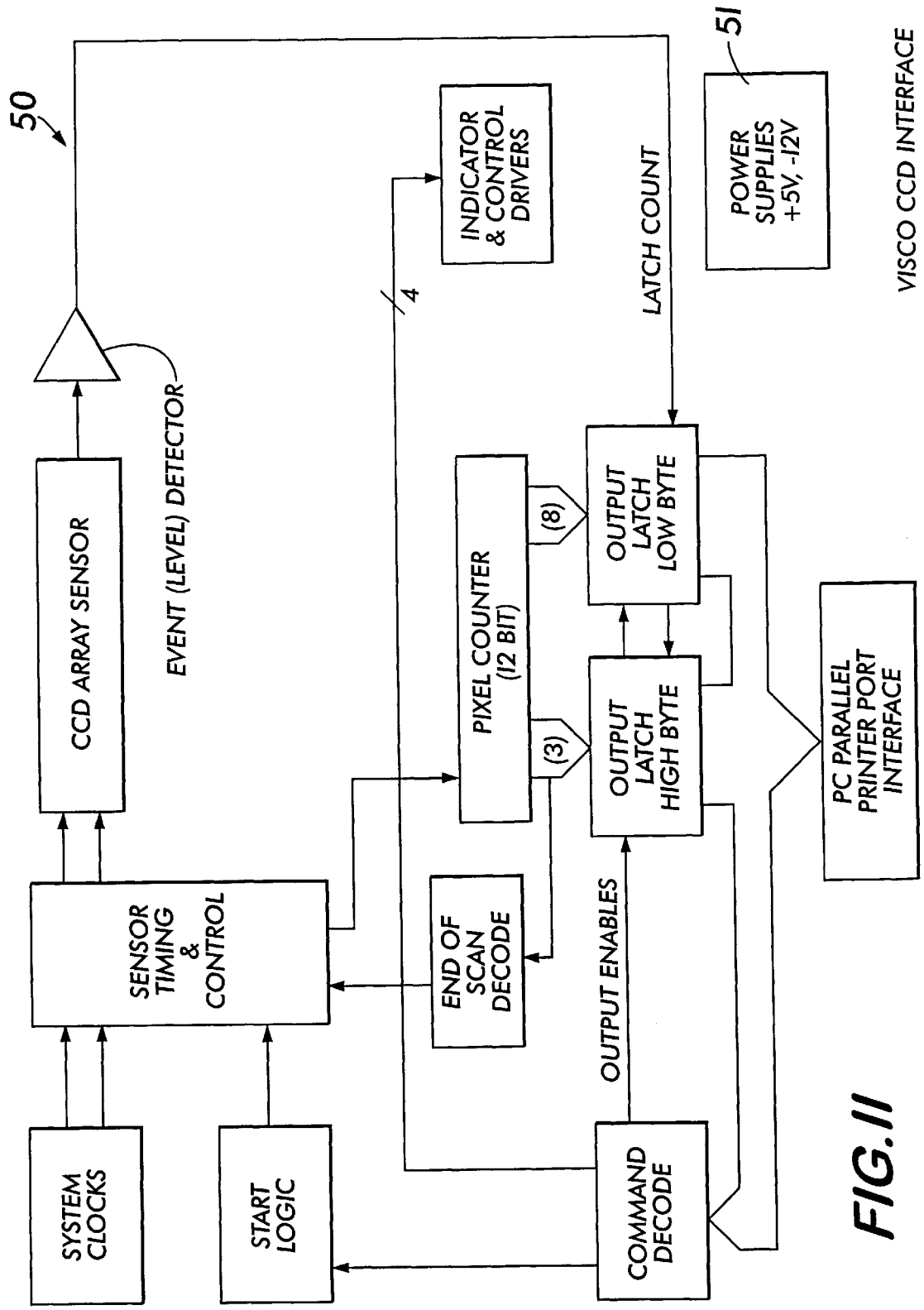
FIG. 11 is a block diagram of a portion of the system shown in FIG. 1, namely, the sensor means.

FIG. 11 is a block diagram of the sensor means 50, while FIG. 12 shows its construction, i.e., a cross-sectional view of it taken along line 12—12 of FIG. 2A but with the support plate 68 already secured to the housing 70. Thus, as can be seen, an exemplary implementation of the sensor means 50 comprises a linear array of illuminators 76 (see FIGS. 2A and 12), rod lenses 106, and sensor chips 108 mounted on a PCB substrate 110. One particularly useful commercial device incorporating their components is the Model SV200A4 sold by Scan Vision, Inc. of San Jose, Calif. The sensor means 50 includes a glass cover 112 that abuts the riser tube 44 when the support 68 is installed, as described earlier. An integrated lens 114 may be disposed on the opposite side of the glass cover 112 to improve viewing by the rod lens 106.

Figure 13:
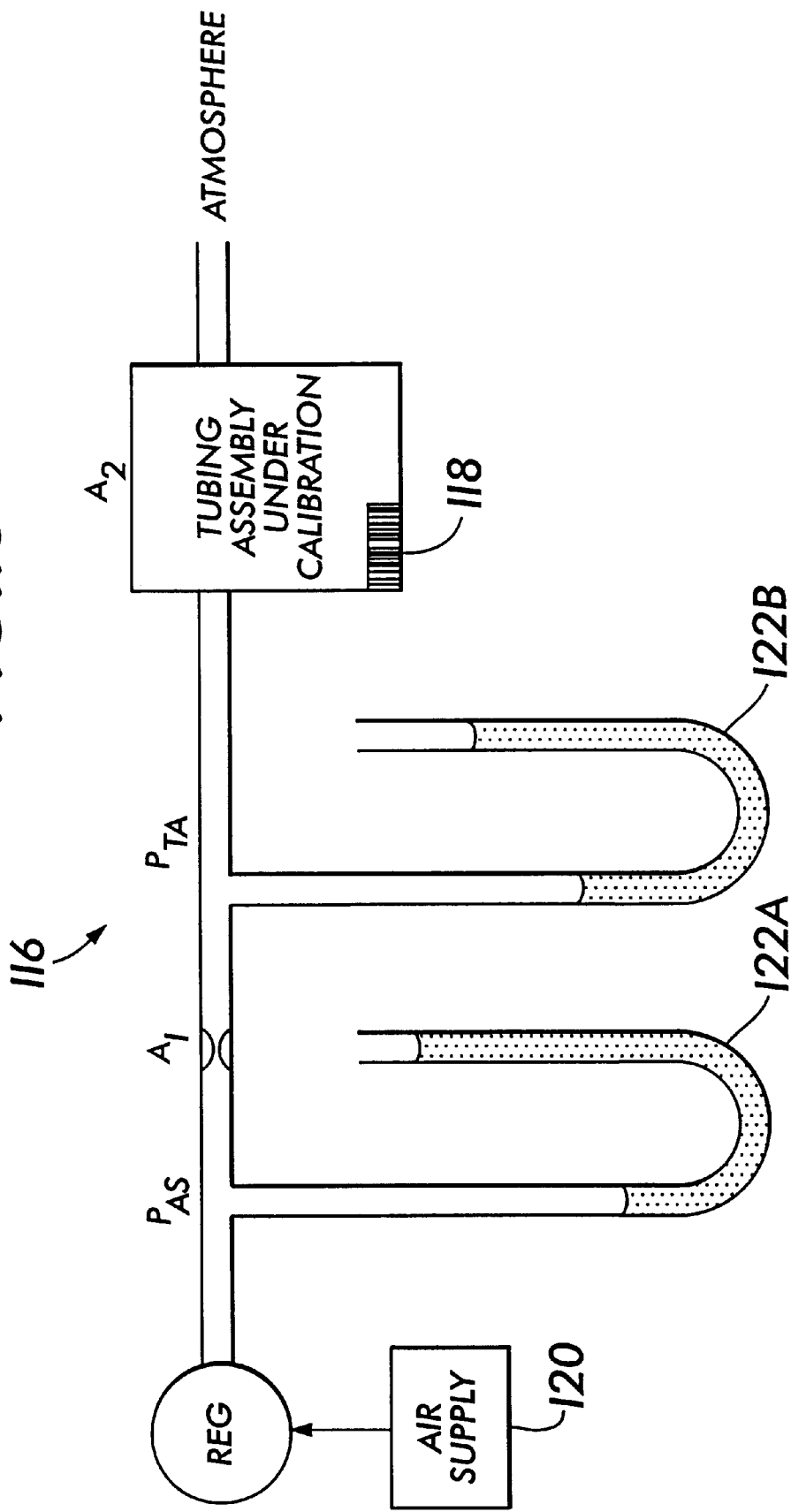
FIG. 13 is an illustration of a calibration test rig for use with the system of FIG. 1.

In order for the system 20 to operate properly, it is necessary for the calculation means 24 to take into account the fluid resistance of the tubing assembly 69 that is mounted in the housing 70. To accomplish that a test rig is utilized. FIG. 13 depicts an exemplary test rig 116 for the tubing assembly 69 of the system 20. A bar code 118 is provided on the support plate 68 (FIGS. 2A and 13) that contains a calibration factor for that particular tubing assembly 69. Thus, just before a viscosity run is made, an automatic scanner 119, coupled to the PC 52, scans the bar code 118 and loads the PC 52 with the particular calibration factor.

To determine the calibration factor, the tubing assembly under calibration, $A_2$, is coupled to the test rig 116, as shown in FIG. 13. An air supply 120 delivers clean dry air at a predetermined pressure, $P_{AS}$ (e.g., 100 psi) that can be regulated (via a regulator REG) down to 30 n $H_2O$. The air supply 120 delivers the flow through a calibrated orifice, $A_1$, having a known resistance. The input of the tubing assembly under test $A_2$ is coupled to the output of $A_1$ and the output of the tubing assembly under test $A_2$ is vented to atmosphere. When the air supply 120 delivers the air flow, depending on the internal fluid resistance of the tubing assembly under test $A_2$, a pressure, $P_{TA}$, appears at the input of the tubing assembly under test, $A_2$. A pair of open-ended manometers 122A and 122B are coupled to the input of $A_1$ and the output of $A_1$, respectively, to monitor $P_{AS}$ and $P_{TA}$, respectively. The ratio $P_{AS}/P_{TA}$ represents the calibration factor. This calibration factor is then encoded into the bar code 118. Thus, each time a tubing assembly 69 is mounted in the housing 70 and the bar code 118 read into the PC 52, the calculation means 24 can make a viscosity determination based on the specific fluid resistance of that mounted tubing assembly 69.

In accordance with another aspect of the present invention and to minimize measurement errors, the system 20 includes the means for controlling the formation of a meniscus 124 (FIG. 3) at the top of the column of transmission fluid 42. In particular, coatings for the riser tube 44 can be introduced to control the surface tension precisely by providing controlled surface energy, thus flattening the meniscus 124. This meniscus 124 can be further controlled by changing the molecular make-up of the riser tube 44, the transmission fluid 41 being used and the gas above the column of fluid 42. Furthermore, to make the surface energy repeatable and predictable, the inner surfaces of riser tube 44 maybe coated by vapor deposition with surfactants, e.g., silicone. By including suitable surfactants, such as silicone, in the extrusions the surfactants migrate to the surfaces in a predictable manner.

An other embodiment (not shown) of the apparatus 20 includes a riser tube 44 that is inclined to increase the sensitivity. In particular, if the riser tube 44 were angled away from a vertical orientation, for each millimeter rise in vertical height of the column of fluid 42, there will be more than one millimeter of displacement of the column of fluid 42 in the riser tube 44.

In accordance with another aspect of the subject invention means 124 (FIG. 2B can be provided to apply vibratory energy to the patient to determine its effect on the patient's blood viscosity and the data developed can then be used to provide customized vibratory therapy to provide beneficial effects. In particular, that aspect of the invention makes use of a vibration source 124 that generates vibratory energy whose amplitude and frequency can be controlled by the operator. This vibratory energy is applied either before or during a viscosity measuring run. Although the vibratory energy is shown in FIG. 2B as being applied to the patient's arm only, it is within the broadest scope of the invention that the vibratory energy can be applied to all or only a portion of the patient's body. The vibration may also be applied to the column of fluid 42, and/or to the capillary tube 26, to obtain a smoother flow of fluid.

Figure 14:
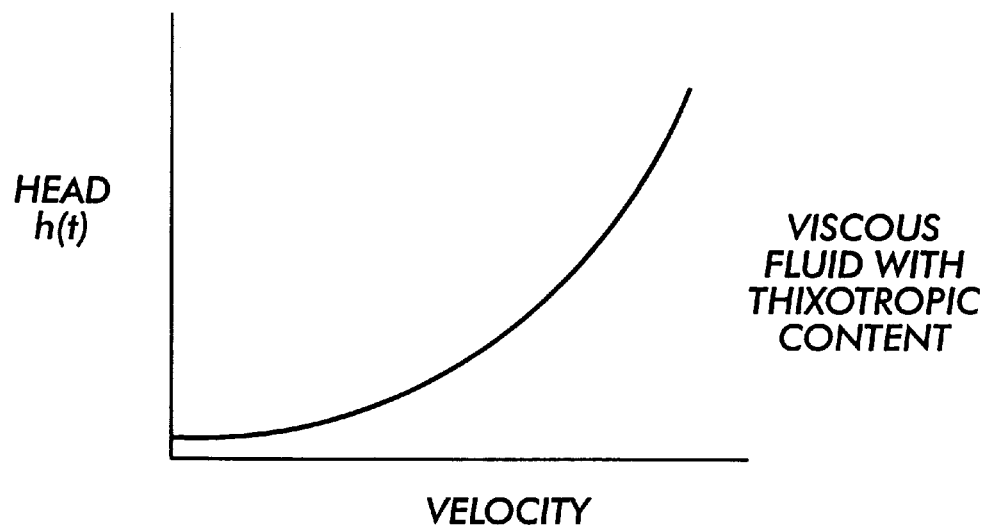
FIG. 14 is a graph similar to FIG. 4 showing the head of the column of fluid plotted versus time to show a thixotropic characteristic of the blood.

Another significant feature of the system 20 is its ability to monitor the level of the column of fluid 42 at which the velocity becomes zero, i.e., the thixotropic point of the blood flow. The thixotropic point represents a shear stress being supported at zero velocity, as graphically depicted in FIG. 14. Presentation of the shear or head at which flow restarts after a set time at zero motion provides an indication of the clotting characteristic of the patient.

It should be understood that the diagnostic software 54 allows for the dynamic effects of deceleration of the column of fluid 42 and for the viscous effects of the various diameters of tubing as the blood 31 and the transmission fluid 41 pass through the system 20.

It should be understood that another implementation of the system 20 comprises a molded or etched channel system as a substitute for the tubing discussed above.

As mentioned earlier, the apparatus 20 has other applications, such as viscosity measurements of other flowable material, e.g., oils, paints and cosmetics.

Without further elaboration, the foregoing will so fully illustrate our invention and others may, by applying current or future knowledge, readily adapt the same for use under various conditions of service.

We claim:

1. Apparatus for determining the viscosity of a flowable material at plural shear rates, said apparatus comprising material receiving means and calculation means, said material receiving means comprising an input tube arranged to be introduced into said material to enable said material to flow therein, said calculation means being coupled to said material receiving means and being arranged to calculate the viscosity of the material within said input tube at plural shear rates and to provide a signal representative thereof, said calculation means comprising a column of fluid and monitoring means, said fluid in said column being arranged to be coupled to the material within said input tube, whereupon said column of fluid changes in height, said monitoring means being arranged to monitor the height of the fluid within said column at plural points along the height thereof as said fluid column changes in height and to calculate the viscosity of the material therefrom;

wherein said flowable material is arranged to flow into said input tube under the force of gravity, whereupon the height of said column of fluid changes;

wherein the relative height of said input tube to said column of fluid is adjustable, whereupon said input tube is disposed above a portion of said column of fluid so that gravity causes said column of fluid to change height; and wherein said apparatus additionally comprises first valve means coupled between said input tube and said column of fluid to selectively enable the flowable material to flow through said input tube to cause said column of fluid to change height.

2. The apparatus of claim 1 wherein said column of fluid is located within a riser tube, said riser tube having a lower portion to which said tube is coupled by said first valve means.

3. The apparatus of claim 2 wherein said riser tube includes an upper portion having a second valve means located thereat, said second valve means being selectable to enable air to flow into said upper portion of said riser tube.

4. The apparatus of claim 3 additionally comprising injector means for selectively introducing said fluid forming said column of fluid into said riser tube.

5. The apparatus of claim 4 wherein said injector means comprises a reservoir of fluid and a plunger.

6. The apparatus of claim 3 wherein said monitoring means comprises sensor means for determining the height of said column of fluid along a multitude of points therealong.

7. The apparatus of claim 6 additionally comprising microprocessor means coupled to said sensor means.

8. The apparatus of claim 6 wherein said sensor means comprises a CCD device.

9. The apparatus of claim 7 wherein said sensor means comprises a CCD device.

10. The apparatus of claim 7 additionally comprising indicator means for providing a visual indication of said viscosity.

11. The apparatus of claim 10 wherein said indicator means comprises a visual display.

12. The apparatus of claim 10 wherein said indicator means comprises a printer.

13. The apparatus of claim 10 wherein said indicator means comprises a visual display and a printer.

14. Apparatus for determining the viscosity of a first flowable material at plural shear rates, said apparatus comprising a first tube, a second elongated tube, a sensor, and computing means, said first tube being arranged for receiving the first flowable material to enable the first flowable material to flow therein, said second tube being coupled to said first tube and being arranged for receipt of a second flowable material, the second flowable material forming a fluid column in said second tube, said fluid column being adapted to change in height, said sensor being arranged to monitor the height of said fluid column at plural points along the length of said second tube as said fluid column changes in height and for providing a first signal indicative thereof, said computing means being responsive to said first signal for calculating the viscosity of the first flowable material at plural shear rates within said first tube and to provide a output signal representative thereof.

15. The apparatus of claim 14 wherein said second flowable material is a different material than the first flowable material.

16. The apparatus of claim 14 wherein said second flowable material is also the first flowable material.

17. The apparatus of claim 14 wherein said sensor comprises a video imaging device.

18. The apparatus of claim 17 wherein said video imaging device comprises a charge coupled device.

19. The apparatus of claim 14 wherein said sensor comprises a charge coupled device.

20. The apparatus of claim 14 wherein said first tube comprises a capillary tube.

21. The apparatus of claim 15 wherein said first tube comprises a capillary tube.

22. The apparatus of claim 14 wherein said height of said fluid column is arranged to change in response to a force applied thereto.

23. The apparatus of claim 22 wherein said apparatus includes means to selectively enable gravity to apply the force to said fluid column, whereupon the height of said fluid column changes in response thereto.

* * * * *